United States Patent [19]

Johnson

[11] Patent Number: 4,612,293
[45] Date of Patent: Sep. 16, 1986

[54] UPGRADING OF SPENT BUTANE ISOMERIZATION CATALYST TO PENTANE ISOMERIZATION CATALYST

[75] Inventor: Marvin M. Johnson, Bartlesville, Okla.

[73] Assignee: Phillips Petroleum Company, Bartlesville, Okla.

[21] Appl. No.: 781,079

[22] Filed: Sep. 27, 1985

[51] Int. Cl.$^4$ ............................................. B01J 27/12
[52] U.S. Cl. ........................................ 502/28; 502/22; 502/27; 502/32; 502/33; 502/36; 502/37; 502/230; 585/749
[58] Field of Search ..................... 502/22, 27, 28, 32, 502/33, 36, 37, 230

[56] References Cited

U.S. PATENT DOCUMENTS

| | | | |
|---|---|---|---|
| 2,479,110 | 8/1949 | Haensel | 196/50 |
| 2,642,384 | 6/1953 | Cox | 196/50 |
| 2,851,398 | 9/1958 | Gornowski | 196/50 |
| 2,939,896 | 6/1960 | Myers | 260/683.68 |
| 3,131,235 | 4/1964 | Asselin | 260/683.68 |
| 3,134,732 | 5/1964 | Kearby et al. | 208/140 |
| 3,140,264 | 7/1964 | Oleck | 502/27 X |
| 3,175,983 | 3/1965 | Mool et al. | 252/416 |
| 3,201,355 | 8/1965 | Kimberlin et al. | 252/411 |
| 3,248,320 | 4/1966 | White et al. | 208/136 |
| 3,717,586 | 2/1973 | Suggitt et al. | 502/230 X |
| 3,787,314 | 1/1974 | Donaldson et al. | 208/60 |
| 3,789,082 | 1/1974 | Cook et al. | 260/683.68 |
| 3,903,195 | 9/1975 | Franck et al. | 260/683.68 |
| 4,209,655 | 6/1980 | Mitsche | 585/664 |

*Primary Examiner*—Patrick P. Garvin
*Attorney, Agent, or Firm*—S. E. Reiter

[57] ABSTRACT

A fluoride-containing platinum on alumina support isomerization catalyst useful for the isomerization of pentane to isopentane can be prepared by a several step treatment of substantially deactivated chloride-containing platinum on alumina support isomerization catalyst. The conversion steps include washing the chloride-containing catalyst to remove substantially all chloride ions, fluorinating the washed material with an aqueous florinating agent, then drying the fluorinated catalyst. Isomerization process employing the catalyst thus prepared is also provided.

9 Claims, No Drawings

UPGRADING OF SPENT BUTANE ISOMERIZATION CATALYST TO PENTANE ISOMERIZATION CATALYST

This invention relates to isomerization processes and catalysts therefore. In one aspect, this invention relates to the rejuvenation of spent isomerization catalysts. In another aspect, this invention relates to the conversion of catalysts useful for the isomerization of $C_4$ hydrocarbons to catalysts useful for the isomerization of $C_5$ hydrocarbons.

BACKGROUND

Platinum on alumina catalysts are useful for the isomerization of saturated hydrocarbons. These catalysts are subject to deactivation as a result of prolonged usage for a variety of reasons. For example, the Physical state of the platinum can change under long term exposure to isomerization conditions. Further, contaminants such as sulfur compounds, metals and water in the feed over an extended period of time tend to deactivate the catalyst. Moreover, carbonization of the catalyst and/or loss of activating catalyst adjuvants can also cause loss of catalyst isomerization activity.

Typically, "spent" (i.e., substantially deactivated) catalysts are processed to extract, separate and recover the platinum values therefrom. The recovered platinum values are then used to prepare fresh catalyst. Such a regeneration process is, however, an expensive operation because of the number of steps involved, the amount of reagents required, etc. A process to readily convert a substantially deactivated isomerization catalyst to a once again active isomerization catalyst would, therefore, be of great benefit to those practicing in the field of hydrocarbon isomerizations.

OBJECTS OF THE INVENTION

An object of the present invention, therefore, is the production of an active isomerization catalyst from a substantially deactivated isomerization catalyst.

Another object of the present invention is the isomerization of pentanes using regenerated butane isomerization catalyst.

These and other objects of the present invention will become apparent from further study of the disclosure and claims provided herein.

STATEMENT OF THE INVENTION

In accordance with the present invention, I have discovered that an active pentane isomerization catalyst can be prepared from a substantially deactivated butane isomerization catalyst by subjecting the butane isomerization catalyst first to a washing step under conditions suitable to remove substantially all chloride ions from the butane isomerization catalyst, then treating the washed catalyst with at least one aqueous fluorinating agent under conditions suitable to provide intimate contact between the alumina support and the fluorinating agent, and finally drying the product of the fluorination step under conditions suitable to produce a substantially water free fluoride containing platinum on alumina support isomerization catalyst.

DETAILED DESCRIPTION OF THE INVENTION

In accordance with the present invention, a process for converting a chloride-containing platinum on alumina isomerization catalyst to a fluoride-containing platinum on alumina support isomerization catalyst is provided which comprises first washing the chloride-containing catalyst with wash medium under conditions suitable to remove substantially all chloride ions therefrom, then treating the washed catalyst with at least one aqueous fluorinating agent under conditions suitable to provide intimate contact between the catalyst and the fluorinating agent, and finally, drying the fluorinated product under conditions suitable to produce a substantially water-free fluoride-containing platinum on alumina support isomerization catalyst.

In accordance with another embodiment of the present invention, process for the isomerization of pentane is provided which comprises contacting a normal-pentane feed under isomerization conditions with a catalyst prepared by first washing a chloride-containing platinum on alumina support isomerization catalyst with wash medium under conditions suitable to remove substantially all chloride ions therefrom, then treating the washed product with at least one aqueous fluorinating agent under conditions suitable to provide intimate contact between the catalyst and the flourinating agent, and finally, drying the fluorinated product under conditions suitable to produce a substantially water-free fluoride-containing platinum on alumina support isomerization catalyst.

The catalyst employed in the practice of the present invention is a platinum on alumina support isomerization catalyst which has been promoted with a chloride containing compound. The preferred catalyst is an aluminum chloride treated platinum on alumina catalyst which is useful for butane isomerization. An especially preferred catalyst for use in the practice of the present invention is a substantially deactivated aluminum chloride treated palladium on alumina catalyst which has been employed for the isomerization of a butane-containing feed.

The first step of the inventive conversion process comprises washing the chloride-containing platinum on alumina support isomerization catalyst with sufficient wash medium under conditions suitable to remove substantially all chloride ions therefrom. Suitable wash media include water as well as organic solvents in which the chloride ions to be removed from the the catalyst are soluble and/or form a complex with the chloride ions such as for example alcohols, chlorinated hydrocarbons, esters, ethers, acids and the like, as well as mixtures of any two or more thereof.

The volume of wash media employed is not critical and can readily be determined by those of skill in the art. Generally, at least enough wash media should be employed to thoroughly contact the catalyst being treated. Preferably, sufficient quantity of wash media is employed to also provide a displacement wash, thus aiding in the removal of the chloride ions. While in theory there is no upper limit as to the amount of wash media which can be employed, preferably less than about 10 volumes of wash media per volume of catalyst will be employed to minimize disposal and/or recycle reconsiderations. Preferably, about 2 to about 6 volumes of wash media per volume of catalyst to be treated will be employed.

The conditions employed for the washing step are not critical and can be readily selected by those of skill in the art. While elevated as well as reduced temperatures can be employed, ambient conditions are preferred since good results are obtained at ambient conditions and minimum energy requirements are placed on the regeneration process when carried out under such conditions.

Suitable fluorinating agents are water soluble fluorine-containing compounds which are capable of reacting with the platinum on alumina support isomerization catalyst, many of which are known by those of skill in the art. Exemplary compounds include HF, and quarternary ammonium fluoride compounds having the formula:

$$(NR_4)HF_2$$

independently H or a carbon radical having 1-6 carbon atoms. HF is presenily preferred because it is readily available, relatively inexpensive, and is capable of essentially quantitative reaction with the washed catalyst which is subjected to the flourinating treatment.

The amount of fluorinating agent employed for the fluorination step can vary widely. Sufficient fluorinating agent should be employed to provide catalyst having isomerization activity after the drying step, while large amounts of fluorination agents are desirably avoided to minimize the need to recycle and/or dispose of excess fluoride. Generally, an amount of fluorinating agent is employed to provide a finished catalyst containing in the range of about 2-10 weight percent fluoride based on the total weight of finished catalyst. Preferably an amount of fluorinating agent is employed to provide a finished catalyst having about 3-10 weight percent fluoride, based on the total weight of finished catalyst.

In accordance with the present invention contacting of the washed catalyst with fluorinating agent is carried out in aqueous solution. Such contacting insures that uniform treatment of the washed catalyst is achieved. While the conditions of fluorinating agent-washed catalyst contacting are not critical, it is preferred for ease of operation that contacting be carried out at ambient conditions. Those of skill in the art recognize, of course, that contacting could be carried out at higher or lower temperatures as well as under reduced or elevated pressures.

The contacting between the fluorinating agent and washed catalyst should be maintained for a sufficient period of time prior to drying to allow reaction to occur between the fluorinating agent and the washed catalyst. Generally, at least about 2 hours are required, with the upper limit being set only by considerations of convenience.

Preferably, contact will be maintained for about 6-48 hours. The length of contacting period required will, of course, vary with the treatment conditions employed, such that for example, longer times would be appropriate at lower temperatures while shorter times would be required at elevated temperatures.

Those of skill in the art recognize that care should be taken to scrub or otherwise suitably treat any off-gases produced in the contacting step or in the subsequent drying step to prevent the release of substantial quantities of fluorides from the process.

Drying of the fluorinated washed catalyst can be carried out by any suitable technique known by those of skill in the art. For example, when large volumes of treating solution are employed, excess liquid can be removed by filtration, decantation or the like. The final, essentially water-free fluoride containing platinum on alumina support isomerization catalyst can then be prepared by drying at elevated temperatures, e.g., 90°-120° C. for a time in the range of about 0.5-6 hours.

In accordance with a particular embodiment of the present invention, process for the isomerization of pentane is provided employing fluoride-containing platinum on alumina support isomerization catalyst prepared as described hereinabove. Thus, a pentane-containing feed is typically contacted with the substantially water-free fluoride-containing platinum on alumina support isomerization catalyst in a plug flow fixed bed reactor. Suitable conditions for carrying out the isomerization process of the present invention include a temperature in the range of about 500°-800° F., pressure in the range of about 500°-800° F., psig, a hydrogen to hydrocarbon feed ratio in the range of about 10:1-1:1, preferably about 2:1, and a liquid hourly space velocity in the range of about 0.2 to 6; preferably about 2.

A further understanding of the present invention and its advantages will be provided by reference to the following nonlimiting examples.

EXAMPLE I

This example describes the regeneration of used butane isomerization catalyst (UOP I-4). Fifty grams of used Butamer catalyst was thoroughly water washed to remove chloride, then oven dried at 110° C. After cooling to room temperature, the dried, washed catalyst was treated with 39 g of 10% aqueous HF solution (about 7.8% F based on the weight of catalyst treated). The washed catalyst and HF solution were maintained in contact at room temperature for about 24 hours, then oven dried at 110° C. for about 4 hours. The dried, fluoride-treated catalyst was then charged to a reactor tube for activation and isomerization studies.

EXAMPLE II

About 16.4 g of the fluorided catalyst prepared as described in Example I were loaded into a tubular reactor, bounded above and below by glass beads. Catalyst was then reduced for about 48 hours at 750° F. and ambient pressure under a trickle flow of hydrogen. Once the catalyst was activated, the reactor was pressured up to about 500 psig with hydrogen, then a mornal-pentane feed was begun. Reaction conditions, feed rates and results are summarized in Table I.

TABLE I

| Sample # | Temp., °F. | Press. psig | H₂ L/hr. | n-C₅ mL/hr. | n-C₅ Conversion | i-C₅ Selectivity |
|---|---|---|---|---|---|---|
| 1 | 700 | 500 | 38 | 56 | 37 | 98 |
| 2 | 730 | 500 | 38 | 56 | 52 | 95 |
| 3 | 760 | 500 | 38 | 57 | 61 | 95 |
| 4 | 760 | 500 | 38 | 59 | 63 | 91 |
| 5 | 760 | 500 | 14 | 27 | 64 | 93 |
| 6 | 760 | 500 | 61 | 91 | 55 | 93 |
| 7 | 760 | 500 | 40 | 63 | 69 | 97 |
| 8 | 760 | 500 | 73 | 107 | 49 | 97 |
| 9 | 760 | 250 | 73 | 107 | 49 | 97 |
| 10 | 760 | 250 | 56 | 82 | 55 | 97 |
| 11 | 760 | 250 | 38 | 60 | 60 | 95 |
| 12 | 760 | 250 | 19 | 26 | 66 | 95 |
| 13 | 760 | 125 | 13 | 29 | 63 | 95 |
| 14 | 760 | 125 | 36 | 55 | 55 | 95 |
| 15 | 760 | 125 | 56 | 81 | 32 | 97 |
| 16 | 760 | 125 | 74 | 112 | 25 | 94 |
| 17 | 760 | 500 | 32 | 61 | 41 | 95 |
| 18 | 760 | 500 | 32 | 29 | 50 | 95 |
| 19 | 760 | 500 | 39 | 61 | 56 | 97 |

The results presented in Table I demonstrate that rejuvenated butane isomerization catalyst is active for isomerization of n-pentane (n-$C_5$) to isopentane (i-$C_5$) over a wide range of feed flow rates, reaction pressures and reaction temperature.

The examples have been provided merely to illustrate the practice of my invention and should not be read so as to limit the scope of my invention or the appended claims in any way. Reasonable variations and modifications not departing from the essence and spirit of my invention, are contemplated to be within the scope of patent protection desired and sought.

I claim:

1. A process for converting a chloride-containing platinum on alumina support isomerization catalyst to a fluoride-containing platinum on alumina support isomerization catalyst which comprises:
   (a) washing said chloride-containing catalyst with wash medium under conditions suitable to remove substantially all chloride ions;
   (b) treating the product of (a) with at least one aqueous fluorinating agent under conditions suitable to provide intimate contact between said alumina support and said fluorinating agent; and
   (c) drying the product of (b) under conditions suitable to produce a substantially water-free fluoride-containing platinum on alumina support isomerization catalyst.

2. A process in accordance with claim 1 wherein said chloride-containing isomerization catalyst is a butane isomerization catalyst.

3. A process in accordance with claim 2 wherein said catalyst is a substantially deactivated butane isomerization catalyst.

4. A process in accordance with claim 1 wherein said wash medium is selected from the group consisting of:

water,
alcohols,
chlorinated hydrocarbons,
esters,
ethers,
organic acids,
and mixtures of any two or more thereof.

5. A process in accordance with claim 1 wherein the volume of wash medium employed varies within the range of about 2–10 volumes per volume of catalyst treated.

6. A process in accordance with claim 1 wherein said fluorinating agent is selected from the group consisting of:

HF, $(NR_4)HF_2$, wherein each R is independently H or a carbon radical having 1–6 carbon atoms, and mixtures of any two or more thereof.

7. A process in accordance with claim 1 wherein the amount of fluorinating agent employed is sufficient to produce a finished catalyst having 2–10 wt % fluoride, based on the total weight of finished catalyst.

8. A process in accordance with claim 1 wherein said conditions suitable to provide intimate contact between said alumina support and said fluorinating agent comprise a temperature in the range of 0°–150° C., for a time of at least one hour.

9. A process in accordance with claim 1 wherein said drying conditions comprise an air atmosphere at a temperature in the range of 90°–120° C. for a time in the range of 0.5–6 hours.

* * * * *